(12) United States Patent
Dias et al.

(10) Patent No.: US 8,946,411 B2
(45) Date of Patent: Feb. 3, 2015

(54) PRODUCTION OF CAPROLACTAM FROM ADIPIC ACID

(71) Applicant: Rennovia, Inc., Menlo Park, CA (US)

(72) Inventors: Eric L. Dias, Belmont, CA (US); Vincent J. Murphy, San Jose, CA (US); James Longmire, San Jose, CA (US); Hong Jiang, Palo Alto, CA (US)

(73) Assignee: Rennovia, Inc., Menlo Park, CA (US)

( * ) Notice: Subject to any disclaimer, the term of this patent is extended or adjusted under 35 U.S.C. 154(b) by 162 days.

(21) Appl. No.: 13/766,705

(22) Filed: Feb. 13, 2013

(65) Prior Publication Data

US 2013/0225785 A1    Aug. 29, 2013

Related U.S. Application Data

(60) Provisional application No. 61/602,533, filed on Feb. 23, 2012.

(51) Int. Cl.
*C07D 201/08*    (2006.01)

(52) U.S. Cl.
USPC ........................... 540/538; 548/400; 564/511

(58) Field of Classification Search
USPC ........................... 540/538; 548/400; 564/511
See application file for complete search history.

(56) References Cited

U.S. PATENT DOCUMENTS

| | | | |
|---|---|---|---|
| 2,351,939 A | | 6/1944 | Drossbach et al. |
| 3,652,549 A | * | 3/1972 | Fujita et al. .................. 540/538 |
| 4,042,490 A | | 8/1977 | Suggitt et al. |
| 4,745,221 A | | 5/1988 | Roffia et al. |
| 4,800,227 A | | 1/1989 | Matson |
| 5,717,089 A | * | 2/1998 | Wolters et al. ................ 540/538 |
| 6,147,208 A | * | 11/2000 | Achhammer et al. ........ 540/538 |
| 6,265,574 B1 | | 7/2001 | Kitamura et al. |
| 6,300,496 B1 | | 10/2001 | Olson et al. |
| 6,362,332 B1 | | 3/2002 | Merger et al. |
| 6,372,939 B1 | | 4/2002 | Bunel et al. |
| 6,462,235 B1 | | 10/2002 | Thiele et al. |
| 6,521,779 B1 | | 2/2003 | Boschat et al. |
| 6,894,163 B2 | | 5/2005 | Tsunoda et al. |
| 8,501,989 B2 | | 8/2013 | Boussie et al. |
| 8,669,397 B2 | | 3/2014 | Boussie et al. |
| 2002/0183478 A1 | | 12/2002 | Fergusson et al. |
| 2010/0145003 A1 | | 6/2010 | Frost |
| 2013/0158255 A1 | | 6/2013 | Archer et al. |
| 2013/0310605 A1 | | 11/2013 | Salem et al. |
| 2013/0331606 A1 | | 12/2013 | Dias et al. |
| 2013/0345473 A1 | | 12/2013 | Archer et al. |

FOREIGN PATENT DOCUMENTS

| | | |
|---|---|---|
| EP | 1251122 A1 | 10/2002 |
| EP | 1975155 A1 | 10/2008 |
| WO | 97/30973 A1 | 8/1997 |
| WO | 00/14062 A1 | 3/2000 |
| WO | 01/96294 A1 | 12/2001 |
| WO | 02/083635 A1 | 10/2002 |
| WO | 2005/051907 A1 | 6/2005 |

OTHER PUBLICATIONS

Invitation to pay additional fees received for PCT Patent Application No. PCT/US2013/025846, mailed on May 7, 2013, 5 pages.
International Search Report and Written Opinion received for PCT Patent Application No. PCT/US2013/025846, mailed on Jul. 1, 2013, 19 pages.
Lan et al., "Effect of Rhenium Component and Preparation Methods of ZrO2 Support on Catalytic Performance of Ru-Re/ZrO2 for Glycerol Hydrogenolysis", Chinese Journal of Catalysis, vol. 30, No. 5, May 2009, pp. 471-478 (English Abstract Only).

\* cited by examiner

*Primary Examiner* — Gregory Listvoyb
(74) *Attorney, Agent, or Firm* — Senniger Powers LLP

(57) ABSTRACT

Processes are disclosed for the conversion of adipic acid to caprolactam employing a chemocatalytic reaction in which an adipic acid substrate is reacted with ammonia and hydrogen, in the presence of particular heterogeneous catalysts and employing unique solvents. The present invention also enables the conversion of other adipic acid substrates, such as mono-esters of adipic acid, di-esters of adipic acid, mono-amides of adipic acid, di-amides of adipic acid, and salts thereof to caprolactam. Solvents useful in the process that do not react with ammonia are also disclosed. Catalyst supports are disclosed which catalyze the reaction of the substrate with ammonia in the absence of added metal. Metals on the catalyst supports comprise ruthenium (Ru), rhodium (Rh), palladium (Pd), osmium (Os), iridium (Ir), and/or platinum (Pt). Heterogeneous catalysts comprising ruthenium (Ru) and rhenium (Re) on titania and/or zirconia supports are also disclosed. Further, disclosed are products produced by such processes, as well as products producible from such products.

32 Claims, No Drawings

PRODUCTION OF CAPROLACTAM FROM ADIPIC ACID

CROSS-REFERENCE TO RELATED APPLICATION

This application claims the benefit under 35 U.S.C. 119(e) of U.S. Provisional Application No. 61/602,533, filed on Feb. 23, 2012, the disclosure of which is hereby incorporated by reference in its entirety.

BACKGROUND

I. Field

The present disclosure relates generally to processes for the chemocatalytic conversion of an adipic acid substrate to epsilon-caprolactam; more specifically, it relates to chemocatalytic conversion of an adipic acid substrate, preferably adipic acid, to intermediates amenable to cyclization to epsilon caprolactam. The processes involve heterogeneous catalysis in the presence of hydrogen, ammonia, particular heterogeneous catalysts and, preferably, particular solvents.

II. Related Art

Epsilon Caprolactam (hereinafter caprolactam) is a chemical intermediate primarily used in the production of nylon 6 fibers and resins.

About 90% of the world's production of caprolactam is based on the intermediate cyclohexanone, which is typically produced by the oxidation of cyclohexane. Caprolactam may also conventionally be produced by the partial hydrogenation of phenol. For the production of caprolactam by either process, cyclohexanone is reacted with a hydroxylamine to produce cyclohexanone oxime followed by a Beckmann rearrangement of the oxime using oleum to yield caprolactam. One disadvantage of the above-described conventional technology is that large amounts of ammonium sulfate—up to 4.5 tons/ton of caprolactam—are produced. Over many years much of the development work directed to manufacturing caprolactam from cyclohexanone has been focused on reducing or even eliminating this byproduct. For example, DSM's HPO Plus™ process (Hydroxylamine Phosphate Oxime), now believed to be used for the production of about 30% of the world's caprolactam, has substantially reduced the quantity of ammonium salt byproduct by as much as two thirds on a ton of salt/ton of product basis. More recently, Sumitomo has commercialized a process that eliminates the production of ammonium sulfate. The process employs an "ammoximation" reaction, whereby cyclohexane is reacted with ammonia and hydrogen peroxide in the presence of a catalyst, and a gas-phase Beckmann rearrangement. See, e.g., U.S. Pat. Nos. 6,265,574, 6,462,235 and 4,745,221. Significantly, one drawback of this process is the cost of hydrogen peroxide.

Other routes, developed primarily in the 1990s, sought to manufacture caprolactam from butadiene or adiponitrile. DSM, working first with DuPont and thereafter with Shell, developed the Altam process (see, e.g., WO 2002/083635), whereby butadiene and carbon monoxide are employed to make caprolactam without ammonium sulfate production. However, this process is still in the final phases of development and employs several complex catalytic reactions—carbonylation, hydroformylation, reductive amination, and cyclization. BASF and DuPont experimented with the production of caprolactam via adiponitrile, although it is not clear whether such processes are currently being practiced. See e.g., U.S. Pat. Nos. 6,372,939, 6,894,163, and 6,521,779; WO 2001/096294.

Toray has developed a photochemical process to convert cyclohexane into cyclohexanone oxime in the presence of nitrosyl chloride and hydrogen chloride, bypassing the use of cyclohexanone or the oximation step. Although this process may provide capital savings, the photochemical process demands significantly more power and the development of large scale photochemical reactors. See chapter devoted to caprolactam in *Kirk-Othmer Encyclopedia of Chemical Technology 5th Edition*, John Wiley and Sons 2001.

In addition to the above-mentioned shortcomings of the processes currently commercially employed and those being announced or developed as potentially viable alternatives, each of these processes suffers fundamentally from the increasing costs and volatility associated with the use of petroleum based feedstocks.

Thus, there remains a need for new, industrially scalable processes for the selective and commercially-meaningful conversion of a renewable feedstock, such as adipic acid derived from biorenewable materials, to caprolactam.

SUMMARY

Briefly, therefore, the present invention is directed to processes for preparing caprolactam from an adipic acid substrate obtained from biorenewable materials. Generally, the process for preparing caprolactam from an adipic acid substrate comprises converting at least a portion of the adipic acid substrate to caprolactam in the presence of ammonia and hydrogen and particular heterogeneous catalysts and, preferably, particular solvents.

The present invention is directed to processes for preparing a caprolactam product by chemocatalytically converting an adipic acid substrate to a caprolactam product, wherein the step of chemocatalytically converting the adipic acid substrate to the caprolactam product comprises reacting the adipic acid substrate with hydrogen and ammonia in the presence of a heterogeneous catalyst and a solvent comprising tert-butanol. The present invention is also directed to processes for preparing a caprolactam product by reacting an adipic acid substrate, hydrogen and ammonia, in the presence of a heterogeneous catalyst comprising at least one metal selected from the group of Ru, Rh, Pd, Pt, Ir, and Os, and mixtures thereof, on a support that is, in the absence of the at least one metal, capable of catalyzing the reaction of the adipic acid substrate and ammonia to produce an amide, and solvent, to convert at least a portion of the adipic acid substrate to the caprolactam product, wherein the adipic acid substrate is a compound of formula I, and wherein the caprolactam product is a compound of formula II

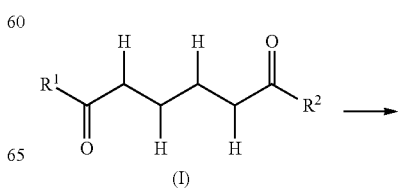

(I)

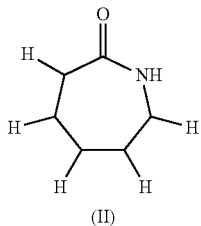

wherein each $R^1$ and $R^2$ is independently hydroxyl, $OR^a$ and $NH_2$; and wherein each $R^a$ is independently selected from the group consisting of hydrogen, alkyl, and a salt-forming ion. In some embodiments, reacting the adipic acid substrate with hydrogen and ammonia in the presence of the heterogeneous catalyst and solvent comprises: a) combining the adipic acid substrate, the ammonia, the heterogeneous catalyst, and solvent; and b) contacting the combined adipic acid substrate, ammonia, heterogeneous catalyst, and solvent with hydrogen. In some embodiments, reacting the adipic acid substrate with hydrogen and ammonia in the presence of the heterogeneous catalyst and solvent comprises: a) combining the adipic acid substrate, ammonia, and solvent; and b) contacting the combined adipic acid substrate, ammonia, and solvent with a heterogeneous catalyst and hydrogen. In some embodiments, reacting the adipic acid substrate with hydrogen and ammonia in the presence of the heterogeneous catalyst and a solvent comprises: a) combining the adipic acid substrate, ammonia, solvent, and heterogeneous catalyst at a temperature between room temperature and about 200° C.; and b) contacting with hydrogen the combined adipic acid substrate, ammonia, solvent, and heterogeneous catalyst. In some embodiments, reacting the adipic acid substrate with hydrogen and ammonia in the presence of the heterogeneous catalyst and solvent comprises: a) contacting the heterogeneous catalyst with hydrogen; b) adding the adipic acid substrate, the ammonia, and the solvent to the heterogeneous catalyst contacted with hydrogen. In some embodiments, reacting the adipic acid substrate with hydrogen and ammonia in the presence of the heterogeneous catalyst and solvent comprises: a) contacting the heterogeneous catalyst with solvent at a temperature in the range of from about room temperature to about 200° C.; and b) contacting the heterogeneous catalyst and solvent with the adipic acid substrate, ammonia, and hydrogen. In some embodiments, reacting the adipic acid substrate with hydrogen and ammonia in the presence of the heterogeneous catalyst and solvent comprises: a) contacting the adipic acid substrate with water; and b) contacting the adipic acid substrate and water with solvent, ammonia, hydrogen, and catalyst. In some embodiments, reacting the adipic acid substrate with hydrogen and ammonia in the presence of the heterogeneous catalyst and solvent comprises: a) combining the adipic acid substrate with water and ammonia; and b) contacting the combination with hydrogen, solvent, and the catalyst. In some embodiments, the adipic acid substrate is derived from a carbohydrate source. In some embodiments, the adipic acid substrate is selected from the group consisting of adipic acid, a mono-ester of adipic acid, a di-ester of adipic acid, a mono-amide of adipic acid, and a di-amide of adipic acid, or salts thereof. In some embodiments, the heterogeneous catalyst comprises ruthenium. In some embodiments, the heterogeneous catalyst comprises a first metal and a second metal, wherein the first metal is Ru and the second metal is selected from the group consisting of Fe, Co, Ni, Cu, W, and Re. In some embodiments, the support of the heterogeneous catalyst comprises a material selected from the group consisting of titanias, zirconias, and mixtures thereof. In some embodiments, the support comprises titania. In some embodiments, the solvent is selected from the group of water, alcohols which do not react with the adipic acid substrate, ethers, and mixtures thereof. In some embodiments, the solvent is selected from the group consisting of tert-butanol, tert-butanol—water mixtures, and tert-butanol—ammonia mixtures. In some embodiments, the solvent comprises up to about 30% by volume water. In some embodiments, the solvent comprises up to about 30% by volume of water and the volume of solvent is equal to or less than about 80% of the total volume of liquid in the reaction. In some embodiments, the molar ratio of first metal to second metal is in the range of from about 100:1 to about 1:10. In some embodiments, the solvent comprises up to about 30% by volume of a solution of ammonia and water. In some embodiments, the ammonia is a solution or a gas. In some embodiments, the reaction is conducted under a partial pressure of hydrogen in the range of from about 200 psi to about 2000 psi. In some embodiments, caprolactam is produced in at least about 50% yield from the adipic acid substrate. In some embodiments, the reaction is carried out as a continuous process. In some embodiments, the reaction is carried out in at least one fixed bed reactor. The present invention is also directed to a process for producing nylon 6 by converting caprolactam produced at least in part by any of the above processes and/or embodiments. The present invention is also directed to caprolactam produced by any of the above processes and/or embodiments.

The present invention is also directed to a process for producing caprolactam from adipic acid by a) converting at least a portion of the adipic acid to at least one amide selected from the group of 6-amino-6-oxohexanoic acid and adipamide in the presence of a metal oxide comprising titania, zirconia, or a mixture thereof; b) reducing the at least one amide to at least one of aminocaproic acid and aminocaproamide; and c) cyclizing at least a portion of the aminocaproic acid and/or aminocaproamide produced from b), above, to caprolactam, wherein at least one of b) and c), above, is carried out in the presence of at least one metal selected from the group of Ru, Pt, Pd, Rh, Ir, and Os. In some embodiments, the at least one metal is Ru. In some embodiments, Re is also present when carrying out at least one of b) and c). In some embodiments, a solvent comprising tert-butanol is present in at least one of a), b), and c). In some embodiments, c) is conducted in the presence of at least one of titania or zirconia, or mixtures thereof.

The present invention is also directed to a catalyst useful for the production of caprolactam comprising ruthenium and rhenium on a support comprising at least one of titania or zirconia. In some embodiments, the support comprises titania. In other embodiments, at least a portion of the titania is in the anatase phase.

DETAILED DESCRIPTION

The following description sets forth exemplary processes, parameters and the like. It should be recognized, however, that such description is not intended as a limitation on the scope of the present invention.

Disclosed herein are processes for the chemocatalytic conversion of adipic acid and derivatives thereof to caprolactam. Generally, the processes for producing caprolactam comprises converting adipic acid and derivatives thereof by processes which employ ammonia, hydrogen, suitable catalysts and, preferably, particular solvents. Adipic acid derivatives used as a substrate in the processes described herein may include, for example, mono-esters of adipic acid, di-esters of adipic acid, mono-amides of adipic acid, di-amides of adipic acid, and salts and mixtures thereof.

The caprolactam prepared in accordance with the disclosed processes may be converted to various other industrially significant chemicals (e.g., nylon 6) according to processes known in the art.

I. Feedstocks

Adipic acid may be obtained from various carbohydrate-containing sources including conventional biorenewable sources such as corn grain (maize), sugar cane, sugar beet, wheat, potato, cassava and rice as well as alternative sources such as energy crops, plant biomass, agricultural wastes, forestry residues, sugar processing residues and plant-derived household wastes. More generally, biorenewable sources that may be used in accordance with the present invention include any renewable organic matter that includes a source of carbohydrates such as, for example, switch grass, miscanthus, trees (hardwood and softwood), vegetation, and crop residues (e.g., bagasse and corn stover). Other sources may include, for example, waste materials (e.g., spent paper, green waste, municipal waste, etc.).

Adipic acid may be produced from biorenewable materials. See, for example, U.S. patent application Ser. Nos. 12/814,188 and 12/814,240, both assigned to the assigned to the present invention.

II. Preparation of Caprolactam from an Adipic Acid Substrate

Applicants have discovered that an adipic acid substrate of formula I may be converted to caprolactam (formula II) according to the following, overall reaction scheme:

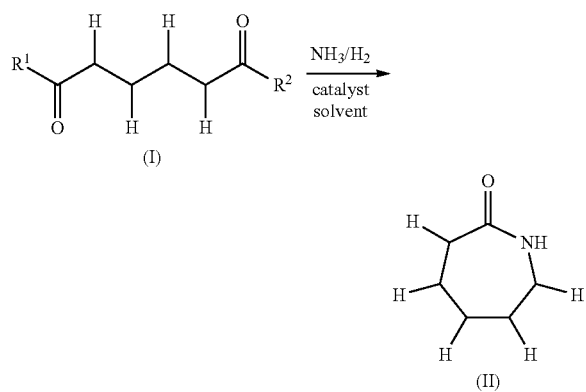

wherein each $R^1$ and $R^2$ is independently hydroxyl, $OR^a$ and $NH_2$; wherein each $R^a$ is independently selected from the group consisting of hydrogen, alkyl, and salt-forming ion. In various preferred embodiments, $R^1$ and $R^2$ are both hydroxyl.

As illustrated above, the adipic acid substrate of formula I can be adipic acid, mono-esters of adipic acid, di-esters of adipic acid, mono-amides of adipic acid, and di-amides of adipic acid, or salts, or mixtures thereof. The adipic acid esters and/or amides may be or comprise the substrate first supplied to a reaction zone or may be generated in situ by, for example, the reaction of adipic acid with ammonia (as more fully described herein).

The overall process involves the reaction of an adipic acid substrate with ammonia and hydrogen, in the presence of at least one of certain heterogeneous catalysts and, preferably, in the presence of particular solvents, to produce caprolactam. One or more additional reaction products may also be produced along the pathway of the overall reaction of adipic acid to caprolactam such as 6-aminocaproic acid, adipamide, mono-amide of adipic acid (6-amino-6-oxohexanoic acid), hexamethyleneimine, mono-ester of adipic acid, di-ester of adipic acid, and 6-aminocaproamide.

Without being bound to a particular reaction mechanism, applicants believe that the adipic acid is converted initially to one or more amides selected from 6-amino-6-oxohexanoic acid and adipamide which, in turn, are reduced to aminocaproic acid and/or 6-aminocaproamide, and the aminocaproic acid and/or aminocaproamide is cyclized to caprolactam (with attendant loss of water and $NH_3$). When the reaction is conducted in a single reaction zone, most (and most preferably all) of any intermediates which may be formed are converted to caprolactam. In such embodiment, the adipic acid product would be reacted in the single reaction zone in the presence of ammonia, hydrogen and a particular catalyst, and one or more useful solvents, to produce caprolactam. It should be understood, however, that the process encompasses embodiments in which the ammonia, hydrogen, and solvents need not be added to a single reactor zone at the same time. Further, although the overall reaction is referred to as the cyclization of an adipic acid substrate to caprolactam, it will be apparent from the disclosure, as more fully described herein, that the reaction may be carried out in several steps in multiple reaction zones of a single reactor or in multiple reactors, wherein each reactor is intended to carry out or focus on one or more of the reactions believed to be occurring along the pathway to the production of caprolactam from the adipic acid substrate.

In accordance with the present invention, the preferred solvent is water. That said, under many reaction conditions, the conversion of adipic acid to the amide is limited by a competing equilibria reaction of the amide with adipic acid. Therefore, the solvent of the reaction is, more typically, a mixture or solution of water and a suitable organic component, which solvent 1) promotes the conversion of adipic acid to the one or more amide intermediates selected from 6-amino-6-oxohexanoic acid, adipamide, or any esters and salts thereof; 2) maintains solubility of the adipic acid substrate, caprolactam, and reaction intermediates; 3) does not react with ammonia under the reaction conditions employed; 4) provide a means for separating the caprolactam from the reaction mixture; and 5) is economically viable. By the phrase "does not react with ammonia" we mean that not more than about 0.1% of the volume of the organic component will be lost to reaction with the ammonia. To those ends, suitable organic components used in combination with water are ethers, amines and cyclic and non-cyclic alcohols whose steric bulk or degree of substitution prevents the molecule from reacting with ammonia: for example, tert-butanol(tert-butyl alcohol), tert-amyl alcohol, 2-ethyl hexanol, tert-butylamine, 2-ethyl-hexylamine, monoglyme(1,2-dimethyoxyethane), diglyme, ethylglyme, ethyldiglyme, triglyme, tetraglyme, polyglymes, and mixtures thereof. When post reaction processing involves the distillation of the solvent from caprolactam, particularly useful organic components are non-cyclic alcohols, especially tert-butanol. When post reaction processing involves the distillation of the caprolactam from the solvent, particularly useful organic solvents are high boiling point organic components such as tetraglyme or polyglyme.

In accordance with the present invention, the solvent comprises water. The total volume of water to the total volume of solvent is at least about 5% and can be, and in some embodiments preferably is, upwards of 20% or 30% or more. In various embodiments, however, for example when post reaction processing involves the distillation of the solvent from caprolactam and the organic component of the solvent is an alcohol, the alcohol is typically about 50% of the total volume of solvent, and may be about 70% or more. In other embodiments of the invention, for example when post reaction processing involves the distillation of the caprolactam from the solvent and the organic component is a high boiling point material such as tetraglyme, the tetraglyme is typically present in an amount of more than about 50% of the total volume of solvent. In those embodiments of the processes wherein the solvent is essentially water, the process is more effective at lower concentrations of adipic acid substrate (e.g., about 10% or less). The solvent may be added to the reaction separately or in combination with the ammonia as, for example, an organic component-water-ammonia mixture or solution. In certain preferred embodiments, the ammonia is added as an ammonia-water solution and the organic component is added separately. The volume percent of ammonia addition as ammonia solution is dictated by the concentration of substrate in the reaction, as will be apparent to those of ordinary skill in this art and as described in more detail herein.

The amount of solvent employed in the processes of the present invention is that amount which is at least sufficient to solubilize the substrate under the process conditions and drive the process toward the exclusive production of amides. Those of ordinary skill in this art can readily determine the quantity of substrate needed to accomplish this objective. Typically, the volume of solvent to the total volume of liquid of the reaction can range from below about 70% to about 90%, with solvent volume at or below about 80% being preferred.

As described above, in various embodiments the ammonia may be added as a solution to the reaction. In certain embodiments, ammonia may be added to the reaction as a gas. In still other embodiments, ammonia may be added to the reaction as both a liquid and a gas. Ratios of ammonia, whether added as a gas or liquid, to adipic acid substrate can vary widely. Generally, a concentration of ammonia relative to adipic acid substrate on a molar basis is at least about 3:1.

The partial pressure of hydrogen is typically at least about 200 pounds per square inch (psig). In various embodiments, the partial pressure of hydrogen is up to about 2000 psig. More typically, the partial pressure of hydrogen is in the range of from about 500 psig to about 1500 psig. In many preferred embodiment, the partial pressure of hydrogen is in the range of from about 750 psig to about 1250 psig.

Catalysts suitable for use in the processes of the present invention are heterogeneous, supported-metal catalysts. Suitable metals of the catalysts of the present invention comprise at least one d-block metal (M1) selected from the group of ruthenium (Ru), rhodium (Rh), palladium (Pd), osmium (Os), iridium (Ir), and platinum (Pt). In various preferred embodiments, the catalyst comprises Ru and/or Rh. Particularly and unexpectedly useful catalysts comprise Ru alone or in combination with particular second metals described hereinafter.

In certain embodiments, the catalyst further includes at least one metal (M2) selected from the group of iron (Fe), cobalt (Co), nickel (Ni), copper (Cu). tungsten (W) and rhenium (Re). Among these metals, Re, W and/or Co are preferred, with Re being especially preferred. For example, when Ru is the d-block metal of the catalyst, the addition of Re has been demonstrated to increase the caprolactam selectivity and yield significantly, as exemplified herein.

In general, the metals may be present in various forms (e.g., elemental, metal oxide, metal hydroxides, metal ions, alloys, etc.). In various preferred embodiments, the metals are present in elemental form. Typically, the total weight of metal(s) of the catalyst is from about 0.2% to about 10% or from about 0.2% to about 8%. Preferably, the total weight of metal is in the range of from about 0.2% to about 5% of the total weight of the catalyst and more preferably no more than about 4% of the total weight of the catalyst.

As described above, the catalyst may comprise a first metal (M1) selected from the above mentioned group and a second metal (M2) selected from the above mentioned group. These metals are deposited onto solid phase supports to produce the heterogeneous catalyst of the present invention. In many preferred embodiments where M1 is Ru, M2 is selected from Co, W and Re, the metals are present on inorganic supports, such as metal oxides (for example, $Al_2O_3$, $TiO_2$, $ZrO_2$, $SiO_2$), zeolites and carbon, among others. The M1:M2 molar ratio may vary. Generally, the molar ratio of M1:M2 is in the range of from about 100:1 to about 1:10. More typically, the ratio is in the range of from about 100:1 to about 1:5, and still more typically in the range of from about 100:1 to about 1:2. When M1 is Ru, the ratio of Ru:M2 is in the range of from about 100:1 to about 1:10 and preferably from about 10:1 to about 1:5.

Catalyst supports useful in combination with the above-described metals to form the heterogeneous, supported catalysts of the present invention can be any of a variety of known supports such as silicas, carbon, zirconias, titanias, aluminas, and zeolites. Applicants have discovered that certain metal oxides typically employed as supports function, without M1 and/or M2 additions, to catalyze the reaction of adipic acid substrate with ammonia to produce heretofore unexpectedly high yields of amide(s) (which are then reduced by the above mentioned M1 and M2 metal additions) and catalyze the cyclization to caprolactam in heretofore unexpectedly high yields. Particular supports which function to catalyze the reaction of the substrate to the amides (including the cyclization to caprolactam) are titanias, zirconias and mixtures thereof. Modified and/or doped titanias and/or zirconias are, of course, useful and may be preferred depending upon the doping metal(s). Titanias (including metal modified/doped titanias), in rutile or anatase form, zirconias modified with titanias, or zirconia/titania mixtures are most preferred. The anatase form of titania is particularly preferred. In particular, for example, Ru-containing, anatase phase, titania-supported catalysts have been shown to produce caprolactam in very high yields, and the reaction can be controlled so as to minimize over-reduction products such as hexamethyleneimine.

The support materials may be modified using methods known in the art such as heat treatment, acid treatment, steam treatment, or by the introduction of a dopant (e.g., metal-doped titanias, metal-doped zirconias (e.g., tungstated-zirconia), or mixtures thereof. The catalyst support may also be treated so as to promote the preferential deposition of suitable metals on the outer surface of the support. The supports may be in a variety of forms, such as powders, pellets, spheres, extrudates, or xerogels.

The metals may be deposited on the supports using procedures known in the art including, but not limited to incipient wetness, ion-exchange, deposition-precipitation, and vacuum impregnation. When two or more metals are deposited on the same support, they may be deposited sequentially or simultaneously. In various embodiments, following metal deposition, the catalyst is dried at a temperature of at least about room temperature, more typically at least about 50° C., and even more typically at least about 120° C., for a period of time of at least about 1 hour, more typically 3 hours or more. In these and other embodiments, the catalyst is dried under sub-atmospheric pressure conditions. In various embodiments, the catalyst is reduced after drying (e.g., by flowing 5% $H_2$ in $N_2$ at 350° C. for 3 hours). Still further, in these and other embodiments, the catalyst is calcined, for example, at a temperature of up to about 600° C. for a period of time (e.g., at least about 3 hours).

The order in which the adipic acid substrate, solvent, ammonia, hydrogen and catalyst are combined to carry out the conversion of an adipic acid substrate to a caprolactam product may vary.

In some embodiments, the adipic acid substrate, the ammonia, the catalyst and the solvent can be first combined, before addition of hydrogen. The resulting reaction mixture may then be heated, subjected to appropriate hydrogen partial pressure and other process conditions such as, for example, flow rate of the combined reaction constituents to the reaction zone(s).

In other embodiments, the adipic acid substrate can be contacted with ammonia and solvent for a period of time, before introduction of hydrogen. In some variations, the adipic acid substrate may be contacted with ammonia and solvent in the presence or absence of the catalyst and/or additional water to the solvent, optionally with heating, and under an atmosphere of air or nitrogen.

In yet other embodiments, the heterogeneous catalyst may first be contacted with hydrogen, before addition of the adipic acid substrate, the ammonia, and the solvent.

In yet other embodiments, the heterogeneous catalyst and solvent can be first combined, before addition of the adipic acid substrate, the ammonia, and the hydrogen. The catalyst and solvent may be combined at elevated temperature to reduce the catalyst reduced in situ, before addition of the adipic acid substrate, the ammonia and the hydrogen.

In other embodiments, the adipic acid substrate can initially be combined only with water, and then the contacted with the solvent, ammonia, hydrogen, and catalyst. In still other embodiments, the adipic acid substrate can initially be combined with water and ammonia (as a gas or a liquid) and thereafter hydrogen, a solvent, and the catalyst may be added (and, optionally, more ammonia).

Generally, the temperature of the reaction mixtures, regardless of the order of addition of reaction constituents, or the conduct of the overall conversion in one or more reactors or reactor zones, is at least about room temperature. Typically, the temperature of the reaction mixture(s) is(are) maintained in the range of from about room temperature (about 20° C.) to about 300° C., and more typically in the range of from about 30° C. to about 200° C. In various preferred embodiments, the temperature(s) is (are) maintained in the range of from about 120° C. to about 180° C.

In general, the cyclization reaction may be conducted in a batch, semi-batch, or continuous reactor design using fixed bed reactors, trickle bed reactors, slurry phase reactors, moving bed reactors, or any other design that allows for heterogeneous catalytic reactions. Examples of reactors may be seen in *Chemical Process Equipment—Selection and Design*, Couper et al., Elsevier 1990, which is incorporated herein by reference. As indicated above, the reaction may be conducted in several reaction zones of a single reactor unit or in several reactors in series or in discontinuous fashion.

The desired reaction products may be recovered from the reaction mixture by one or more conventional methods known in the art including, for example, solvent extraction, crystallization, or evaporative processes such as distillation. For example, the reaction product withdrawn from the reactor may comprise caprolactam, small amounts of hexamethyleneimine, some unreacted substrate, organic constituent of the solvent, ammonia, and water, which reaction product may be processed, for example, as follows: initially, the reaction mixture can be subjected to distillation to remove the lights (organic constituent of the solvent if, for example, an alcohol such as tert-butanol, water and ammonia) and hexamethyleneimine followed by recovery of caprolactam from the remaining constituents (e.g., unreacted substrate and uncyclized intermediates). The remaining components of the product mixture (e.g., unreacted substrate and uncyclized intermediates) can be recycled to the reactor. In an alternative embodiment, caprolactam produced in the process can be recovered by distillation from a reaction product mixture comprising a high boiling point organic solvent constituent after the lights (water and ammonia) are removed.

The processes described herein produce caprolactam with unexpected selectivity compared to the other products that may be produced in the reaction, such as hexamethyleneimine and hexamethylenediamine. Those of ordinary skill in this art will be able to modify the reaction conditions, order of addition, and reaction constituents described herein to optimize the process being employed, all in accordance with the teachings hereof. As illustrated in the examples below, selectivity of the reaction to caprolactam from the substrate/intermediates along the reaction pathway has been demonstrated to exceed 80% or, in many instances, 90%. Moreover, in various embodiments of the present invention, the yield of caprolactam from adipic acid is at least about 50% and preferably at least about 55%. Further, the use of tert-butanol/aqueous ammonia as the solvent has been shown to further enhance the selectivity and yield of caprolactam from adipic acid.

III. Downstream Chemical Products

Caprolactam formed by the processes described herein may be further used for the preparation of polyamides by means generally known in the art. Specifically, caprolactam may be further used for the preparation of nylon 6. See e.g., Kohan, Mestemacher, Pagilagan, Redmond, "Polyamides" in *Ullmann's Encyclopedia of Industrial Chemistry*, Wiley-VCH, Weinheim, 2005.

When introducing elements of the present invention or the preferred embodiments(s) thereof, the articles "a", "an", "the" and "said" are intended to mean that there are one or more of the elements. The terms "comprising", "including" and "having" are not intended to be inclusive and use of such terms mean that there may be additional elements other than the listed elements.

In view of the above, it will be seen that the several objects of the invention are achieved and other advantageous results attained.

As various changes could be made in the above compositions and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

EXAMPLES

The following non-limiting examples are provided to further illustrate the present invention.

Example 1

Preparation of Caprolactam from Adipic Acid 20 mg of 2.02% Ru/ST31119 ($TiO_2$) catalyst (surface area=75 $m^2/g$) was dispensed into a 1.2 mL vial containing 2.92 mg of adipic acid. To the vial was added 0.2 mL of a solvent mixture containing 10% by volume aqueous NH₄OH (about 15M NH₃ in H₂O) in 1,2-dimethoxyethane. The vial was transferred to a pressure reactor which was then sealed, purged with nitrogen and pressurized with hydrogen to 900 psig at room temperature. The reactor was agitated and heated to 160° C. for 180 minutes. After 180 minutes, the reactor was cooled to room temperature, vented, and purged with nitrogen prior to being unsealed. Caprolactam yield was determined using a calibrated HPLC method with UV detection at 218 nm. The yield of caprolactam was 57.5%.

Example 2

Preparation of Caprolactam from Adipic Acid

Caprolactam was produced from adipic acid using the protocol described in Example 1 above, except the catalyst used was a 2.02% Ru/ST61120 (TiO₂) catalyst. The yield of caprolactam was 53.6%.

Example 3

Preparation of Caprolactam from Adipic Acid

Caprolactam was produced from adipic acid using the protocol described in Example 1 above, except that 1,4-dioxane was used in lieu of 1,2-dimethoxyethane. The yield of caprolactam was 49.7%.

Example 4

Preparation of Caprolactam from Adipic Acid

Preparation of Supported Ru and Supported Ru/M2 Catalysts

Approximately 20 mg of powdered support was dispensed to a 1 mL glass vial followed by addition of a suitably concentrated aqueous solution of Ru(NO)(NO₃)₃ (Alfa Aesar). The volume of ruthenium solution was matched to equal the pore volume of the support weighed into the vial. The catalyst mixture was then agitated via a multi-tube vortexer to impregnate the support. Supports were TiO₂, as ST31119 and ST61120, both Saint Gobain (SA=103.2 and 130 m²/g, respectively); see Tables 1 and 2), and Zirconia XZO 1247 from MEL Chemicals. The supported catalysts were dried overnight at 60° C. under a dry air purge.

To the dried supported ruthenium catalyst was added a suitably concentrated aqueous solution of a second metal, M2 (M2=Co or Re obtained from Strem and Sigma-Aldrich, respectively). The volume of M2 solution was matched to equal the pore volume of the support weighed into the vial. The catalyst mixture was then agitated via a multi-tube vortexer to impregnate the support.

Ru/Support catalysts and Ru/M2/Support catalysts were dried at 60° C. for at least 3 hr, under N₂ or dry air purge, before being reduced for 3 hr under forming gas (5% H₂ and 95% N₂) at 250° C.

Catalyst Screening Procedure

Catalysts prepared as described above were transferred to 1 mL glass vials within a 96-well reactor insert. Each vial contained 2.92 mg (0.02 mmol) of adipic acid. To select vials within the array was added 0.1 or 0.2 mL of a solvent mixture consisting of 10% v/v aqueous NH₄OH (ca. 15M NH₃ in H₂O) in tert-butyl alcohol. Some vials also received TiO₂ (ST31119, SA=103 m2/g, Saint-Gobain) as an additive (See Table 3). The vials were covered with a Teflon pinhole sheet, a silicone pinhole mat, and a steel gas diffusion plate. The reactor insert was placed in a pressure vessel and purged three times with N₂. The pressure vessel was then charged twice with ammonia gas to 10 psig with venting after each pressurization step. The reactor was finally charged to 10 psig with ammonia gas and placed on a shaker at 500 rpm for 15 minutes at ambient temperature. The reactor was then brought to 825 psig with hydrogen and placed back on the shaker at 800 rpm and heated to 160° C.

After 120 minutes, the reactor was cooled to room temperature, vented, and purged with nitrogen prior to being unsealed. The samples were diluted with water, mixed, and then centrifuged to separate catalyst particles. Aliquots were removed from the supernatant and diluted further with dilute aqueous HCl for analysis by HPLC. Product yield was determined using a calibrated HPLC method with Charged Aerosol (CAD) and UV detection (218 nm). Product yield and selectivity is listed in Tables 1-3, below. The following equation was used to calculate product selectivity: Selectivity=[(CL+ACA)/(CL+ACA+HMI)]*100, where CL=Caprolactam yield, ACA=Aminocaproic Acid Yield, HMI=Hexamethyleneimine yield

TABLE 1

Adipic Acid to Caprolactam using Ru/M2/Titania ST31119 Catalysts

| Entry | Catalyst (wt % Ru/ wt % M2) | M2 precursor | Substrate Conc. (mM) | Caprolactam Yield (%) | Aminocaproic Acid Yield (%) | Hexamethyleneimine Yield (%) | Selectivity |
|---|---|---|---|---|---|---|---|
| 1 | 1.5% Ru | None | 100 | 49.4 | 0.6 | 4.9 | 91.1 |
| 2 | 2% Ru | None | 100 | 56.5 | 1.3 | 9.0 | 86.5 |
| 3 | 2% Ru/ 3.5% Re | HReO₄ | 100 | 57.5 | 1.5 | 4.6 | 92.8 |
| 4 | 2% Ru/ 1.1% Co | Co(NO₃)₂ | 100 | 45.0 | 0.6 | 2.8 | 94.3 |

TABLE 2

Adipic Acid to Caprolactam using Ru/M2/Titania ST61120 Catalysts

| Entry | Catalyst (wt % Ru/ wt % M2) | M2 precursor | Substrate Conc. (mM) | Caprolactam Yield (%) | Aminocaproic Acid Yield (%) | Hexamethyleneimine Yield (%) | Selectivity |
|---|---|---|---|---|---|---|---|
| 5 | 1.5% Ru | None | 100 | 48.3 | 1.9 | 5.7 | 89.8 |
| 6 | 2% Ru | None | 100 | 52.6 | 3.4 | 11.0 | 83.6 |

TABLE 2-continued

Adipic Acid to Caprolactam using Ru/M2/Titania ST61120 Catalysts

| Entry | Catalyst (wt % Ru/ wt % M2) | M2 precursor | Substrate Conc. (mM) | Caprolactam Yield (%) | Aminocaproic Acid Yield (%) | Hexamethyleneimine Yield (%) | Selectivity |
|---|---|---|---|---|---|---|---|
| 7 | 2% Ru/ 3.5% Re | HReO$_4$ | 100 | 54.8 | 2.9 | 5.7 | 91.1 |
| 8 | 2% Ru/ 1.1% Co | Co(NO$_3$)$_2$ | 100 | 44.6 | 1.3 | 3.2 | 93.5 |

TABLE 3

Adipic Acid to Caprolactam using Ru/M2/Zirconia XZO 1247 Catalysts

| Entry | Catalyst (wt % Ru/ wt % M2) | M2 precursor | Substrate Conc. (mM) | Caprolactam Yield (%) | Aminocaproic Acid Yield (%) | Hexamethyleneimine Yield (%) | Selectivity |
|---|---|---|---|---|---|---|---|
| 9 | 2% Ru | None | 200 | 32.2 | 0.52 | 20.5 | 61.5 |
| 10 | 2% Ru/ 1.4% Re | HReO$_4$ | 200 | 28.5 | 1.9 | 3.1 | 90.8 |
| 11[b] | 2% Ru/ 1.4% Re | HReO$_4$ | 200 | 44.6 | 1.6 | 3.7 | 92.6 |

[b]10 mg of Titania ST31119 was added as an additional reaction constituent

The results from Tables 1-3 demonstrate that caprolactam can be produced in high yield with limited over-reaction product being produced, particularly in the presence of Ru/Re catalysts and at selectivities exceeding 90%. Moreover, as is apparent from the results the intermediate amine is substantially absent from the final reaction mixture further evidencing substantially full conversion of the amine to caprolactam. Also notable from the results of reported in Table 3 is the additional effect of employing TiO$_2$ as an additional reaction constituent in the process.

Example 5

Efficacy of TiO$_2$ and ZrO$_2$ Supports in Production of Amides

To illustrate the unexpected beneficial effects of TiO$_2$ and ZrO$_2$ in the process of the present invention, particularly with regard to the pathway by which caprolactam is believed to be produced from adipic acid, 20 mg of support and 2.92 mg of Adipic Acid were dispensed into a 1 mL glass vial contained in a 96-well reactor insert. Next was added 0.2 mL of a solvent mixture containing 10% v/v aqueous NH$_4$OH (ca. 15M NH$_3$ in H$_2$O) in tert-BuOH or a solvent mixture containing 10% v/v H$_2$O in tert-BuOH. The vial was covered with a Teflon pinhole sheet, a silicone pinhole mat, and a steel gas diffusion plate. The reactor insert was placed in a pressure vessel and purged three times with N$_2$. The pressure vessel was then charged twice with ammonia gas to 10 psig with venting after each pressurization step. The reactor was finally charged to 10 psig with ammonia gas and placed on a shaker at 500 rpm for 15 minutes at ambient temperature. The reactor was then brought to 825 psig with hydrogen and placed back on the shaker at 800 rpm and heated to 160° C. for the specified time (30 or 120 minutes).

The reactor was cooled to room temperature, vented, and purged with nitrogen prior to being unsealed. The samples were diluted with water, mixed, and then centrifuged to separate support particles. Aliquots were removed from the supernatant and diluted further with dilute aqueous HCl for analysis by HPLC. Product yield was determined using a calibrated HPLC method with Charged Aerosol Detection (CAD). The yield of 6-amino-6-oxohexanoic acid and adipamide is listed below in Tables 4 and 5. As illustrated, titania and zirconia, without added catalytic metal, have a dramatic effect on the production of the intermediates from which caprolactam is ultimately produced from adipic acid. For comparison, Table 6 illustrates the relative ineffectiveness of employing other known support materials.

TABLE 4

Adipic Acid to 6-amino-6-oxohexanoic Acid and Adipamide using Titania Supports

| Entry | Support | Supplier | Solvent | Rxn Time (min) | 6-amino-6-oxohexanoic Yield (%) | Adipamide Yield (%) |
|---|---|---|---|---|---|---|
| 1 | ST31119 (SA = 103 m2/g) | Saint-Gobain | 10% H$_2$O in t-BuOH | 30 | 28.7 | 40.5 |
| 2 | ST31119 (SA = 103 m2/g) | Saint-Gobain | 10% NH$_4$OH in t-BuOH | 30 | 24.7 | 47.0 |
| 3 | ST31119 (SA = 103 m2/g) | Saint-Gobain | 10% H$_2$O in t-BuOH | 120 | 30.5 | 42.2 |
| 4 | ST31119 (SA = 103 m2/g) | Saint-Gobain | 10% NH$_4$OH in t-BuOH | 120 | 29.0 | 54.0 |

TABLE 4-continued

Adipic Acid to 6-amino-6-oxohexanoic Acid and Adipamide using Titania Supports

| Entry | Support | Supplier | Solvent | Rxn Time (min) | 6-amino-6-oxohexanoic Yield (%) | Adipamide Yield (%) |
|---|---|---|---|---|---|---|
| 5 | ST31119 (SA = 40 m2/g) | Saint-Gobain | 10% H$_2$O in t-BuOH | 30 | 34.4 | 52.0 |
| 6 | ST31119 (SA = 40 m2/g) | Saint-Gobain | 10% NH$_4$OH in t-BuOH | 30 | 22.0 | 69.3 |
| 7 | ST31119 (SA = 40 m2/g) | Saint-Gobain | 10% H$_2$O in t-BuOH | 120 | 34.9 | 54.1 |
| 8 | ST31119 (SA = 40 m2/g) | Saint-Gobain | 10% NH$_4$OH in t-BuOH | 120 | 26.0 | 68.7 |
| 9 | ST31119 (SA = 81 m2/g) | Saint-Gobain | 10% H$_2$O in t-BuOH | 30 | 29.2 | 44.1 |
| 10 | ST31119 (SA = 81 m2/g) | Saint-Gobain | 10% NH$_4$OH in t-BuOH | 30 | 25.1 | 55.8 |
| 11 | ST31119 (SA = 81 m2/g) | Saint-Gobain | 10% H$_2$O in t-BuOH | 120 | 30.4 | 49.1 |
| 12 | ST31119 (SA = 81 m2/g) | Saint-Gobain | 10% NH$_4$OH in t-BuOH | 120 | 28.3 | 59.3 |
| 13 | ST61120 | Saint-Gobain | 10% H$_2$O in t-BuOH | 30 | 27.4 | 37.4 |
| 14 | ST61120 | Saint-Gobain | 10% NH$_4$OH in t-BuOH | 30 | 24.1 | 43.0 |
| 15 | ST61120 | Saint-Gobain | 10% H$_2$O in t-BuOH | 120 | 30.3 | 39.6 |
| 16 | ST61120 | Saint-Gobain | 10% NH$_4$OH in t-BuOH | 120 | 28.7 | 46.7 |

TABLE 5

Adipic Acid to 6-amino-6-oxohexanoic Acid and Adipamide using Zirconia Supports

| Entry | Support | Supplier | Solvent | Rxn Time (min) | 6-amino-6-oxohexanoic Yield (%) | Adipamide Yield (%) |
|---|---|---|---|---|---|---|
| 1 | XZO1247 | MEL Chemicals | 10% H$_2$O in t-BuOH | 30 | 65.0 | 15.7 |
| 2 | XZO1247 | MEL Chemicals | 10% NH$_4$OH in t-BuOH | 30 | 48.5 | 38.9 |
| 3 | XZO1247 | MEL Chemicals | 10% H$_2$O in t-BuOH | 120 | 53.8 | 30.5 |
| 4 | XZO1247 | MEL Chemicals | 10% NH$_4$OH in t-BuOH | 120 | 28.4 | 64.9 |
| 5 | XZO1501 | MEL Chemicals | 10% H$_2$O in t-BuOH | 30 | 58.1 | 22.3 |
| 6 | XZO1501 | MEL Chemicals | 10% NH$_4$OH in t-BuOH | 30 | 32.1 | 54.9 |
| 7 | XZO1501 | MEL Chemicals | 10% H$_2$O in t-BuOH | 120 | 41.4 | 38.9 |
| 8 | XZO1501 | MEL Chemicals | 10% NH$_4$OH in t-BuOH | 120 | 28.3 | 64.4 |
| 9 | Z10074 | Sud-Chemie | 10% H$_2$O in t-BuOH | 30 | 54.7 | 6.5 |
| 10 | Z10074 | Sud-Chemie | 10% NH$_4$OH in t-BuOH | 30 | 68.1 | 18.5 |
| 11 | Z10074 | Sud-Chemie | 10% H$_2$O in t-BuOH | 120 | 61.7 | 19.0 |
| 12 | Z10074 | Sud-Chemie | 10% NH$_4$OH in t-BuOH | 120 | 44.9 | 44.3 |
| 13 | Z1628 | DKKK | 10% H$_2$O in t-BuOH | 30 | 63.1 | 21.6 |
| 14 | Z1628 | DKKK | 10% NH$_4$OH in t-BuOH | 30 | 48.7 | 40.2 |
| 15 | Z1628 | DKKK | 10% H$_2$O in t-BuOH | 120 | 45.2 | 41.7 |
| 16 | Z1628 | DKKK | 10% NH$_4$OH in t-BuOH | 120 | 26.4 | 61.1 |

TABLE 6

Adipic Acid to 6-amino-6-oxohexanoic Acid and Adipamide using Other Known Catalyst Supports

| Entry | Support | Supplier | Solvent | Rxn Time (min) | 6-amino-6-oxohexanoic Yield (%) | Adipamide Yield (%) |
|---|---|---|---|---|---|---|
| 1 | Al$_2$O$_3$ Catalox SBa-90 | Sasol | 10% NH$_4$OH in t-BuOH | 120 | 44.9 | 5.7 |
| 2 | Al$_2$O$_3$ Catalox SBa-200 | Sasol | 10% NH$_4$OH in t-BuOH | 30 | 23.2 | 1.2 |
| 3 | Al$_2$O$_3$ SA6175 | Saint-Gobain | 10% NH$_4$OH in t-BuOH | 120 | 38.6 | 6.1 |
| 4 | Al$_2$O$_3$ SA6175 | Saint-Gobain | 10% NH$_4$OH in t-BuOH | 30 | 22.9 | 1.4 |
| 5 | Carbon ROX 0.8 | Norit | 10% NH$_4$OH in t-BuOH | 120 | 28.8 | 2.7 |
| 6 | Carbon ROX 0.8 | Norit | 10% NH$_4$OH in t-BuOH | 30 | 12.8 | — |
| 7 | KA-160* | Sud-Chemie | 10% NH$_4$OH in t-BuOH | 120 | 36.9 | 4.7 |
| 8 | KA-160* | Sud-Chemie | 10% NH$_4$OH in t-BuOH | 30 | 21.5 | 1.0 |
| 9 | K10* | Sud-Chemie | 10% NH$_4$OH in t-BuOH | 120 | 43.0 | 7.3 |
| 10 | K10* | Sud-Chemie | 10% NH$_4$OH in t-BuOH | 30 | 25.8 | 1.9 |
| 11 | CP811C-300 | Zeolyst | 10% NH$_4$OH in t-BuOH | 120 | 39.2 | 5.2 |

TABLE 6-continued

Adipic Acid to 6-amino-6-oxohexanoic Acid and Adipamide using Other Known Catalyst Supports

| Entry | Support | Supplier | Solvent | Rxn Time (min) | 6-amino-6-oxohexanoic Yield (%) | Adipamide Yield (%) |
|---|---|---|---|---|---|---|
| 12 | CP811C-300 | Zeolyst | 10% NH$_4$OH in t-BuOH | 30 | 21.8 | 1.2 |
| 13 | CBV720 | Zeolyst | 10% NH$_4$OH in t-BuOH | 120 | 48.0 | 8.5 |
| 14 | CBV720 | Zeolyst | 10% NH$_4$OH in t-BuOH | 30 | 21.3 | 1.4 |

*montmorillonite

We claim:

1. A process for preparing a caprolactam product, the process comprising chemocatalytically converting an adipic acid substrate to a caprolactam product, wherein the step of chemocatalytically converting the adipic acid substrate to the caprolactam product comprises reacting the adipic acid substrate with hydrogen and ammonia in the presence of a heterogeneous catalyst and a solvent comprising tert-butanol.

2. A process for preparing a caprolactam product, the process comprising:
reacting an adipic acid substrate, hydrogen, and ammonia, in the presence of a heterogeneous catalyst comprising at least one metal selected from the group of Ru, Rh, Pt, Pd, Ir, and Os, and mixtures thereof, on a support that is, in the absence of the at least one metal, capable of catalyzing the reaction of the adipic acid substrate and ammonia to produce an amide, and solvent, to convert at least a portion of the adipic acid substrate to the caprolactam product, wherein the adipic acid substrate is a compound of formula I, and wherein the caprolactam product is a compound of formula II

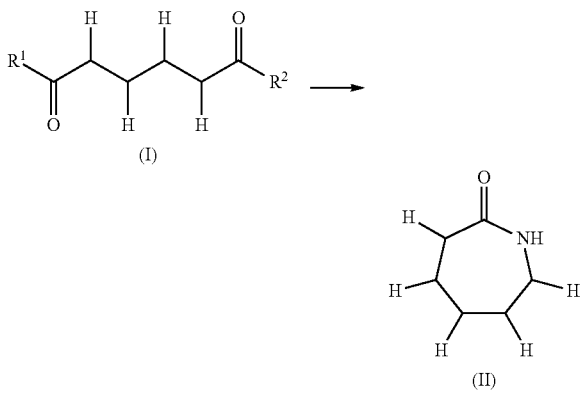

wherein each $R^1$ and $R^2$ is independently $OR^a$ and $NH_2$;
wherein each $R^a$ is independently selected from the group consisting of hydrogen, alkyl, and a salt-forming ion.

3. The process of claim 1, wherein the heterogeneous catalyst comprises at least one metal selected from the group of Ru, Rh, Pt, Pd, Ir, and Os, and mixtures thereof, on a support.

4. The process of claim 2 or 3, wherein the metal weight of the at least one metal selected from the group of Ru, Rh, Pt, Pd, Ir, and Os, and mixtures thereof is from about 0.2 wt. % to about 10% of the total weight of the catalyst.

5. The process of claim 2 or 3, wherein the metal weight of the at least one metal selected from the group of Ru, Rh, Pt, Pd, Ir, and Os, and mixtures thereof is from about 0.2 wt. % to about 5% of the total weight of the catalyst.

6. The process of claim 2 or 3, wherein the heterogeneous catalyst comprises Ru and further comprises a second metal selected from the group consisting of Fe, Co, Ni, Cu, W, and Re.

7. The process of claim 1 or 2, wherein the reaction is conducted at a temperature in the range of from about 20° C. to about 200° C.

8. The process of claim 6, wherein the support of the heterogeneous catalyst comprises a material selected from the group consisting of titanias, zirconias, and mixtures thereof.

9. The process of claim 6, wherein the support of the heterogeneous catalyst comprises titania.

10. The process of claim 1 or 2, the adipic acid substrate is derived from a carbohydrate source.

11. The process of claim 1 or 2, wherein the adipic acid substrate comprises adipic acid.

12. The process of claim 1 or 2, wherein the heterogeneous catalyst comprises ruthenium.

13. The process of claim 2 or 3, wherein the support of the heterogeneous catalyst comprises a material selected from the group consisting of titanias, zirconias, and mixtures thereof.

14. The process of claim 13, wherein the support comprises titania.

15. The process of claim 2, wherein the solvent is selected from the group of water, alcohols which do not react with the adipic acid substrate, ethers, and mixtures thereof.

16. The process of claim 15, wherein the solvent is selected from the group consisting of tert-butanol, tert-butanol—water mixtures, and tert-butanol—ammonia mixtures.

17. The process of claim 6, wherein the molar ratio of Ru to second metal is in the range of from about 100:1 to about 1:10.

18. The process of claim 1 or 2, wherein the ammonia a gas.

19. The process of claim 1 or 2, wherein the reaction is conducted under a partial pressure of hydrogen in the range of from about 200 psi to about 2000 psi.

20. The process of claim 2, wherein caprolactam is produced in at least about 50% yield from the adipic acid substrate.

21. The process of claim 2, wherein the reaction is carried out as a continuous process.

22. The process of claim 2, wherein the reaction is carried out in at least one fixed bed reactor.

23. A process for producing nylon 6, the process comprising:
preparing a caprolactam product in accordance with the process of claim 1 or 2, and
converting at least a portion of the caprolactam product into nylon 6.

24. A process for producing caprolactam from adipic acid, the process comprising the steps of:

a) converting at least a portion of the adipic acid to at least one amide selected from the group of 6-amino-6-oxo-hexanoic acid and adipamide in the presence of a metal oxide comprising titania, zirconia, or a mixture thereof,
b) reducing the at least one amide to at least one of aminocaproic acid and aminocaproamide, and
c) cyclizing at least a portion of the aminocaproic acid and/or aminocaproamide produced from b), above, to caprolactam, wherein at least one of b) and c), above, is carried out in the presence of at least one metal selected from the group of Ru, Pt, Pd, Rh, Ir, and Os.

25. The process of claim 24 wherein the at least one metal is Ru.

26. The process of claim 25 wherein Re is also present when carrying out at least one of b) and c).

27. The process of claim 25 wherein a solvent comprising tert-butanol is present in at least one of a), b), and c).

28. The process of claim 24 wherein c) is conducted in the presence of at least one of titania or zirconia, or mixtures thereof.

29. A catalyst comprising ruthenium and rhenium on a support comprising titania, wherein the catalyst is capable of catalyzing the conversion of adipic acid to caprolactam.

30. The catalyst of claim 29 wherein the metal weight of ruthenium and rhenium is from about 0.2 wt. % to about 5% of the total weight of the catalyst and the ratio of ruthenium or rhenium is from about 10:1 to about 1:5.

31. The catalyst of claim 30 wherein at least a portion of the titania is in the anatase phase.

32. The process of claim 2 or 3, wherein the adipic acid substrate comprises adipic acid;
the heterogeneous catalyst comprises ruthenium; the weight of ruthenium is from about 0.2 wt. % to about 5% of the total weight of the catalyst; the support of the heterogeneous catalyst comprises a material selected from the group consisting of titanias, zirconias, and mixtures thereof; and the reaction is conducted at a temperature from about 20° C. to about 200° C.

\* \* \* \* \*